(12) United States Patent
Jun (10) Patent No.: US 9,414,791 B2
(45) Date of Patent: Aug. 16, 2016

(54) X-RAY PHOTOGRAPHING APPARATUS (75) Inventor: Jin-Hwan Jun, Anyang-si (KR)

(73) Assignee: GENORAY CO., LTD., Seongnam-Si, Gyeonggi-Do (KR)

(*) Notice: Subject to any disclaimer, the term of this patent is extended or adjusted under 35 U.S.C. 154(b) by 82 days.

(21) Appl. No.: 14/382,319

(22) PCT Filed: Jul. 13, 2012

(86) PCT No.: PCT/KR2012/005568
§ 371 (c)(1),
(2), (4) Date: Aug. 31, 2014

(87) PCT Pub. No.: WO2013/137523
PCT Pub. Date: Sep. 19, 2013

(65) Prior Publication Data
US 2015/0117600 A1 Apr. 30, 2015

(30) Foreign Application Priority Data
Mar. 12, 2012 (KR) .................. 10-2012-0025072

(51) Int. Cl.
A61B 6/14 (2006.01)
A61B 6/00 (2006.01)
A61B 6/06 (2006.01)

(52) U.S. Cl.
CPC ... *A61B 6/14* (2013.01); *A61B 6/06* (2013.01); *A61B 6/4435* (2013.01); *A61B 6/587* (2013.01)

(58) Field of Classification Search
CPC ............. H05G 1/02; A61B 6/06; A61B 6/14; A61B 6/587; A61B 6/4435

USPC ...................... 378/38–40, 193–197
See application file for complete search history.

(56) References Cited

U.S. PATENT DOCUMENTS

| 4,783,793 A | 11/1988 | Virta et al. |
| 4,974,243 A * | 11/1990 | McArdle ................ A61B 6/501 378/180 |
| 2004/0190678 A1 | 9/2004 | Rotondo et al. |
| 2009/0245461 A1 | 10/2009 | Lee |
| 2010/0074403 A1 | 3/2010 | Inglese et al. |
| 2010/0128840 A1 | 5/2010 | Cha |
| 2012/0039436 A1 | 2/2012 | Bothorel et al. |

FOREIGN PATENT DOCUMENTS

| JP | 9-215682 | 8/1997 |
| JP | 2004-208754 A | 7/2004 |
| KR | 10-2010-0023785 A | 3/2010 |

* cited by examiner

Primary Examiner — Courtney Thomas
(74) Attorney, Agent, or Firm — Revolution IP, PLLC (57) ABSTRACT Disclosed is an X-ray photographing apparatus comprising: an X-ray generator for generating X-rays; an X-ray detector for detecting the X-rays discharged from the X-ray generator; and a collimator for permitting only a portion of the X-rays to pass through and blocking the rest X-rays, wherein the apparatus further comprising a support means for supporting the X-rays generator and the X-ray detector and varying heights of the X-ray generator and the X-ray detector, wherein the X-ray generator and the X-ray detector are arranged facing each other at respective left and right sides with respect to the support means for supporting the X-ray generator and the X-ray detector so as to achieve a weight balance, and the support means has an X-ray path through which the X-rays generated by the X-ray generator pass without interference.

6 Claims, 7 Drawing Sheets

X-RAY PHOTOGRAPHING APPARATUS

CROSS REFERENCE TO PRIOR APPLICATIONS

This application is a National Stage Application of PCT International Patent Application No. PCT/KR2012/005568 filed on Jul. 13, 2012, under 35 U.S.C. §371, which claims priority to Korean Patent Application No. 10-2012-0025072 filed on Mar. 12, 2012, which are all hereby incorporated by reference in their entirety.

TECHNICAL FIELD

The present invention relates to an X-ray photographing apparatus, and more particularly, to an X-ray photographing apparatus in which mechanical stability of the X-ray photographing apparatus that irradiates the head and/or teeth with X-rays and detects the X-rays, thus acquiring an image of the head and/or an image of the teeth, is secured.

BACKGROUND ART

In general, photographing technology using X-rays is one of important technologies used to acquire an image of an inside of the human body in a medical field at the present time, and an image capturing apparatus using the X-rays is an X-ray photographing apparatus.

Such an X-ray photographing apparatus is being applied in the form of various apparatuses in order to capture an internal organ of the human body, a structure of teeth, or an image of the head.

In particular, the X-ray photographing apparatus used in a dental clinic is used to acquire an image required for a dental surgical procedure, such as orthodontics or treatment of the teeth, by capturing an image of the teeth and an image of the head.

Figure 1:
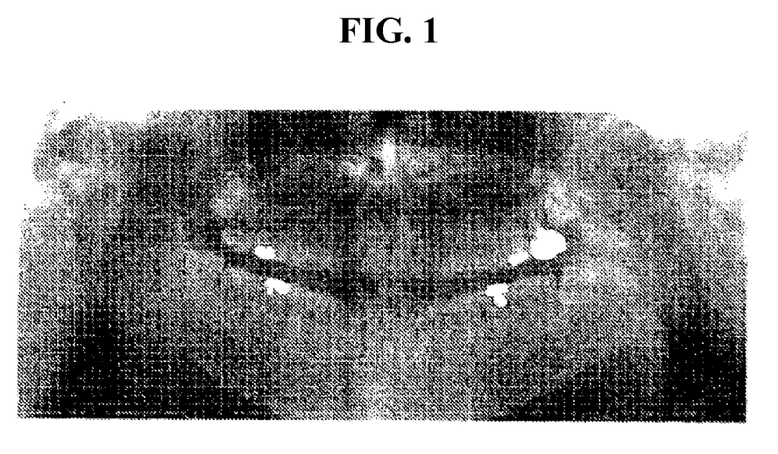
FIG. 1 is an image of the teeth captured by an X-ray photographing apparatus for a dental clinic according to the related art.
Figure 2:
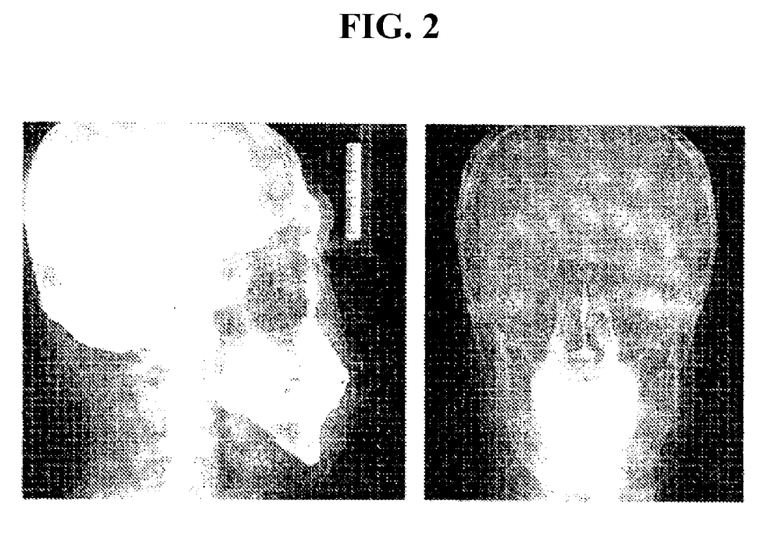
FIG. 2 is an image of the head captured by the X-ray photographing for a dental clinic according to the related art.

An image of the teeth captured in a panorama manner using an X-ray photographing apparatus in the related art is shown in FIG. 1, and an image of the head is shown in FIG. 2.

Meanwhile, a configuration of the X-ray photographing apparatus according to the related art disclosed in Korean Patent Registration No. 10-0904187 that has been already filed by the Applicant of the present application and has obtained a patent will be described with reference to FIGS. 3 through 6. The X-ray photographing apparatus according to the related art includes an X-ray generator 10 that generates X-rays, an X-ray detector 20 that detects the X-rays, and a collimator 80 that permits only a portion of the X-rays to pass through and blocks the rest X-rays.

Figure 3:
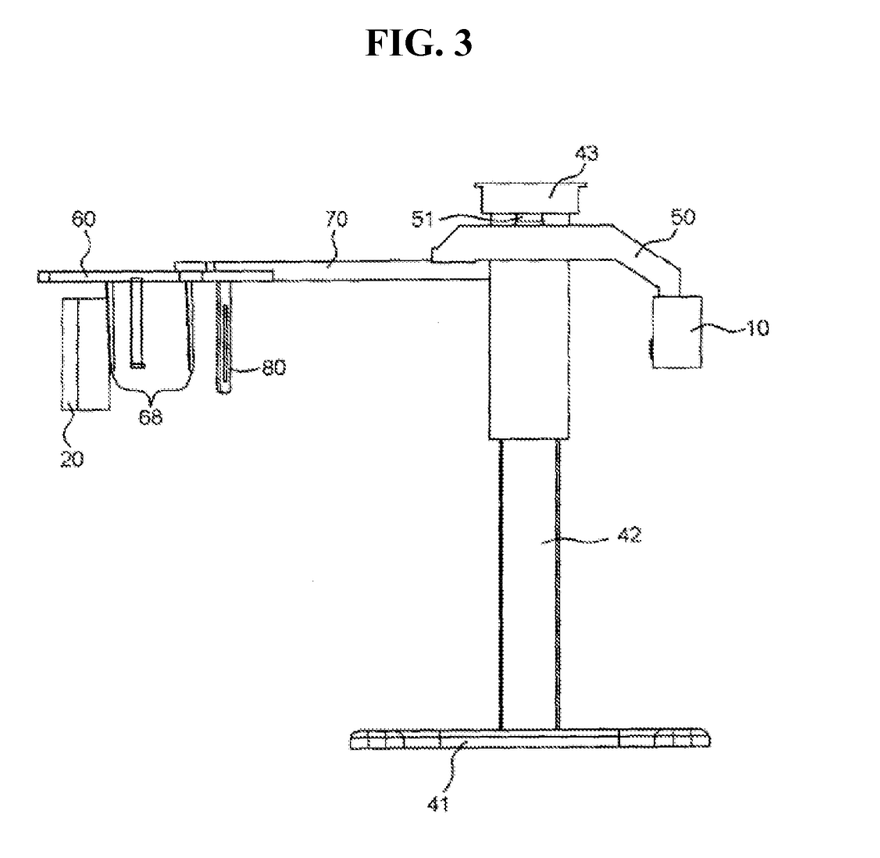
FIG. 3 is a front view of an embodiment of an X-ray photographing apparatus according to the related art.
Figure 4:
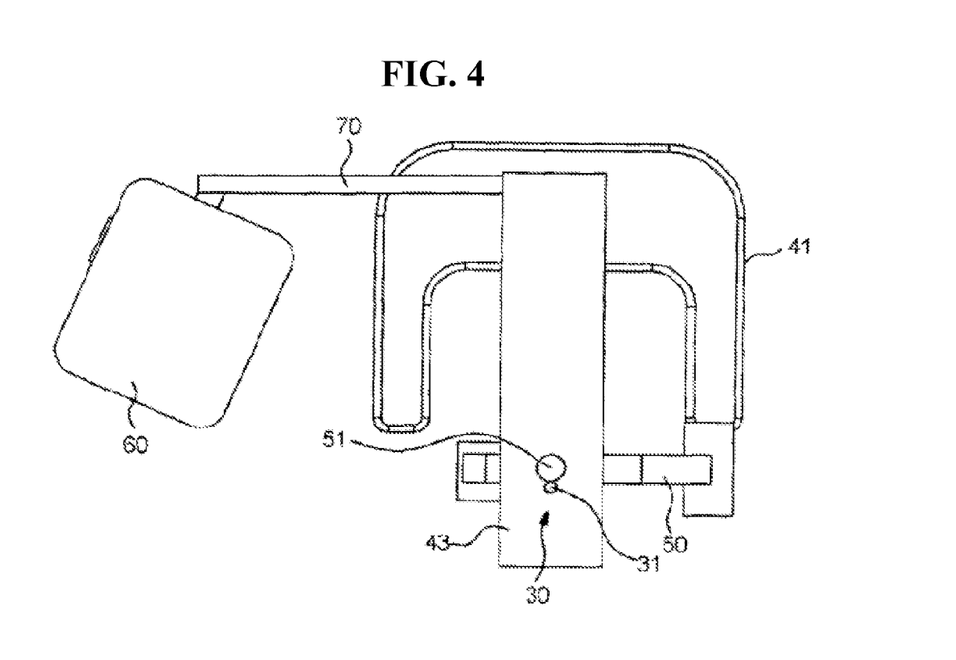
FIG. 4 is a plan view of the X-ray photographing apparatus illustrated in FIG. 3.

The X-ray generator 10 is configured to make a turning movement along a curve path by rotating and driving a rotation driving unit 30 and radiates the X-rays. To this end, the X-ray generator 10 includes an X-ray light source (not shown) for generating the X-rays.

The X-ray detector 20 is mounted on a cephalo-acquisition portion that is disposed on a support body 60 so as to acquire an image of the head. In order to acquire an image of the teeth captured in a panorama manner, the X-ray detector 20 is mounted on a panorama acquisition portion.

The collimator 80 that is moved in parallel to the X-ray detector 20, is disposed on the support body 60. A slit is formed in the collimator 80 so that only a portion of the X-rays irradiated by the X-ray generator 10 reaches the X-ray detector 20. Thus, the collimator 80 permits only a portion of the X-rays irradiated by the X-ray generator 10 to pass through via the slit and blocks the rest X-rays so that damage of the human body caused by the X-rays is minimized Here, the slit is formed in the middle of the collimator 80 to be long in a lengthwise direction.

The X-ray photographing apparatus includes a base 41, a lift 42 installed perpendicular to the base 41, and a driving portion housing 43 disposed on an upper portion of the lift 42, which are a basic skeletal structure for mounting the X-ray generator 10 and the X-ray detector 20.

An actuator for the rotation driving unit 30, for example, a motor 31 is built in the driving portion housing 43 and generates a rotational force. A rotation body 50 is connected to the body unit. In greater detail, the rotation body 50 is coupled to a lower side of the driving portion housing 43.

The rotation body 50 is connected to the rotation driving unit, i.e., a rotation shaft 51 rotated by the motor 31, and the X-ray generator 10 is disposed on the rotation body 50, is moved integrally with the rotation body 50 and irradiates the head and/or teeth with the X-rays.

The X-ray photographing apparatus includes an image output portion (not shown) that outputs an image of a subject according to signals detected by the X-ray detector.

Figure 5:
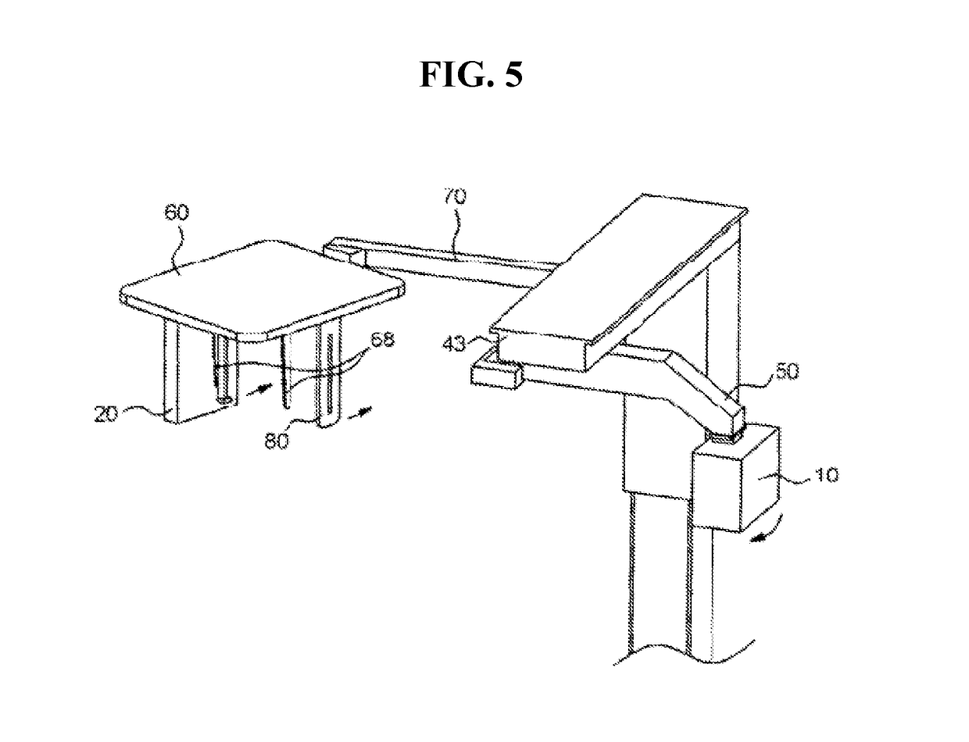
FIG. 5 is a perspective view of a head image capturing portion of the X-ray photographing apparatus of FIG. 3.
Figure 6:
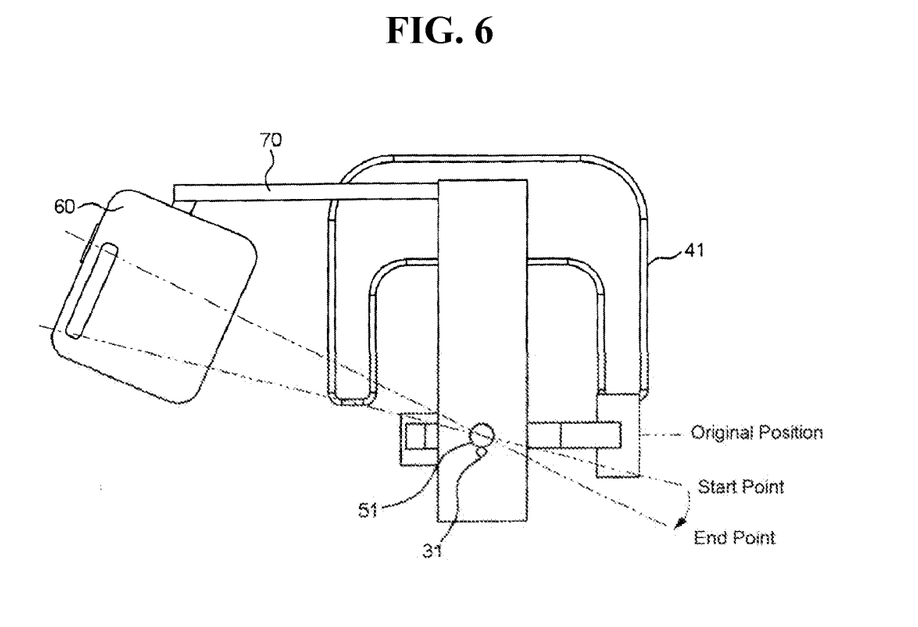
FIG. 6 illustrates a movement of an X-ray generator and an X-ray detector when an image of the head is captured using the X-ray photographing apparatus according to the related art of FIG. 3.

An alignment portion for aligning the human face so as to scan a line of the head may be disposed on the support body 60. The alignment portion includes a pair of ear fixing portions 68 through which both ears of the head face each other.

The X-ray photographing apparatus should acquire an image of the head when the X-ray detector 20 for acquiring an image of the head is distant from the X-ray light source by 1800 mm. This is to minimize distortion of the image.

However, the X-ray photographing apparatus in the related art has the following problems.

That is, in the X-ray photographing apparatus in the related art, the cephalo-acquisition portion is provided at an end of a support arm that extends to one side on an axis of the lift 42, and the panorama acquisition portion is mounted in front of the X-ray photographing apparatus. The X-ray photographing apparatus according to the related art is shown in a plan view of FIG. 4 or 6 from an upward direction. Since the cephalo-acquisition portion and the panorama acquisition portion are leaning to one side around the base 41, this is very disadvantageous in terms of a weight balance, and the X-ray photographing apparatus according to the related art is designed to have an unstable structure.

This is to prevent an interfered portion from being generated on a path of the X-ray light source when the X-ray photographing apparatus according to the related art is compacted while a distance from the X-ray light source to the X-ray detector 20 of the cephalo-acquisition portion is maintained at 1800 mm. However, as described above, this is unstable in terms of the weight balance.

Of course, a structure of the X-ray photographing apparatus in which the panorama acquisition portion and the cephalo-acquisition portion are separated from each other and two dedicated lifts are used, may be considered. However, in such a case, the lifts should be separately disposed at the respective panorama acquisition portion and the cephalo-acquisition portion when the panorama acquisition portion and the cephalo-acquisition portion are separated from each other. Thus, this causes an increase in production cost of a product, and there are many problems that a system is complicated so as to simultaneously control the heights of the X-ray light source and the cephalo-acquisition portion according to human height.

Thus, an X-ray photographing apparatus having an improved structure in which instability of the weight balance of the conventional X-ray photographing apparatus described above is removed so that mechanical stability of the X-ray photographing apparatus is improved and the X-ray photographing apparatus is capable of being compacted and an operation system of the X-ray photographing apparatus is simplified, is in urgent need of development.

DISCLOSURE

Technical Problem

The present invention is directed to providing an X-ray photographing apparatus in which mechanical stability of the X-ray photographing apparatus that irradiates the head and/or teeth with X-rays and detects the X-rays, thus acquiring an image of the head and/or an image of the teeth, is improved, thereby achieving improved reliability of a product.

The present invention is also directed to providing an X-ray photographing apparatus having an improved structure in which mechanical stability of the X-ray photographing apparatus is improved, the X-ray photographing apparatus is capable of being compacted, thereby improving spatial utility and an operation system of the X-ray photographing apparatus is simplified.

Technical Solution

One aspect of the present invention provides an X-ray photographing apparatus including: an X-ray generator for generating X-rays; an X-ray detector for detecting the X-rays discharged from the X-ray generator; and a collimator for permitting only a portion of the X-rays to pass through and blocking the rest X-rays, wherein the apparatus further including a support means for supporting the X-rays generator and the X-ray detector and varying heights of the X-ray generator and the X-ray detector, wherein the X-ray generator and the X-ray detector may be arranged facing each other at respective left and right sides with respect to the support means for supporting the X-ray generator and the X-ray detector so as to achieve a weight balance, and the support means may have an X-ray path through which the X-rays generated by the X-ray generator pass without interference.

The support means may include a lift base, a lift guide fixed to a top surface of the lift base, and a lift that is supported by the lift guide, is installed to be elevatable in a lengthwise direction of the lift guide and has a path through which the X-rays pass.

The X-ray path may be a through hole formed in a surface of the lift in a penetration structure, or the X-ray path may be an escape groove formed by a bent structure of the lift.

Advantageous Effects

An X-ray photographing apparatus according to the present invention has the following effects.

According to the present invention, mechanical stability of the X-ray photographing apparatus that irradiates the head and/or teeth with X-rays and detects the X-rays, thus acquiring an image of the head and/or an image of the teeth, can be improved.

That is, according to the present invention, since a weight balance of the X-ray photographing apparatus is improved, mechanical stability of the X-ray photographing apparatus is improved and thus reliability of a product is improved.

Also, according to the present invention, as the weight balance is improved, a lift, of which a smaller eccentric load than that of the conventional X-ray photographing apparatus is considered, can be designed and applied so that production cost of the X-ray photographing apparatus can be reduced.

Furthermore, according to the present invention, mechanical stability of the X-ray photographing apparatus is improved, and the X-ray photographing apparatus is capable of being compacted, thereby improving spatial utility and an operation system of the X-ray photographing apparatus is simplified.

DESCRIPTION OF DRAWINGS

FIGS. 9($a$) and 9($b$) are front views of a modified example of portion "A" of FIG. 7.

BEST MODE OF THE INVENTION

Hereinafter, an X-ray photographing apparatus according to the present invention will be described in detail with reference to FIGS. 7 through 9.

Figure 7:
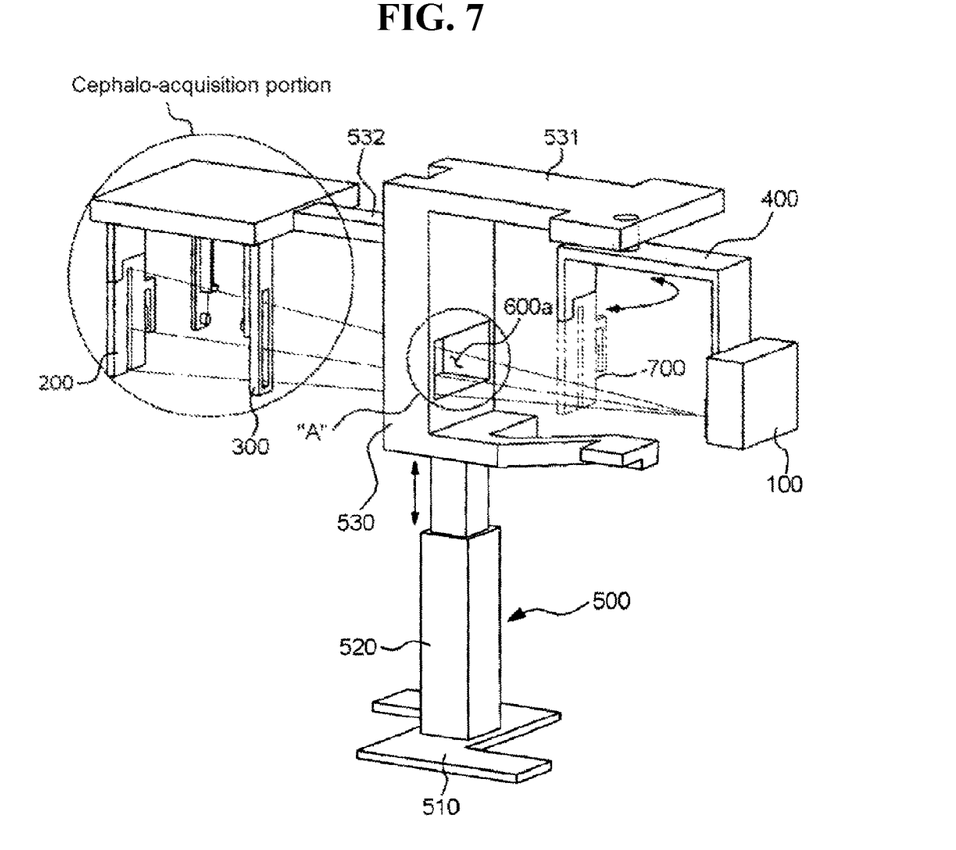
FIG. 7 is a perspective view of a configuration of an X-ray photographing apparatus according to an embodiment of the present invention.
Figure 8:
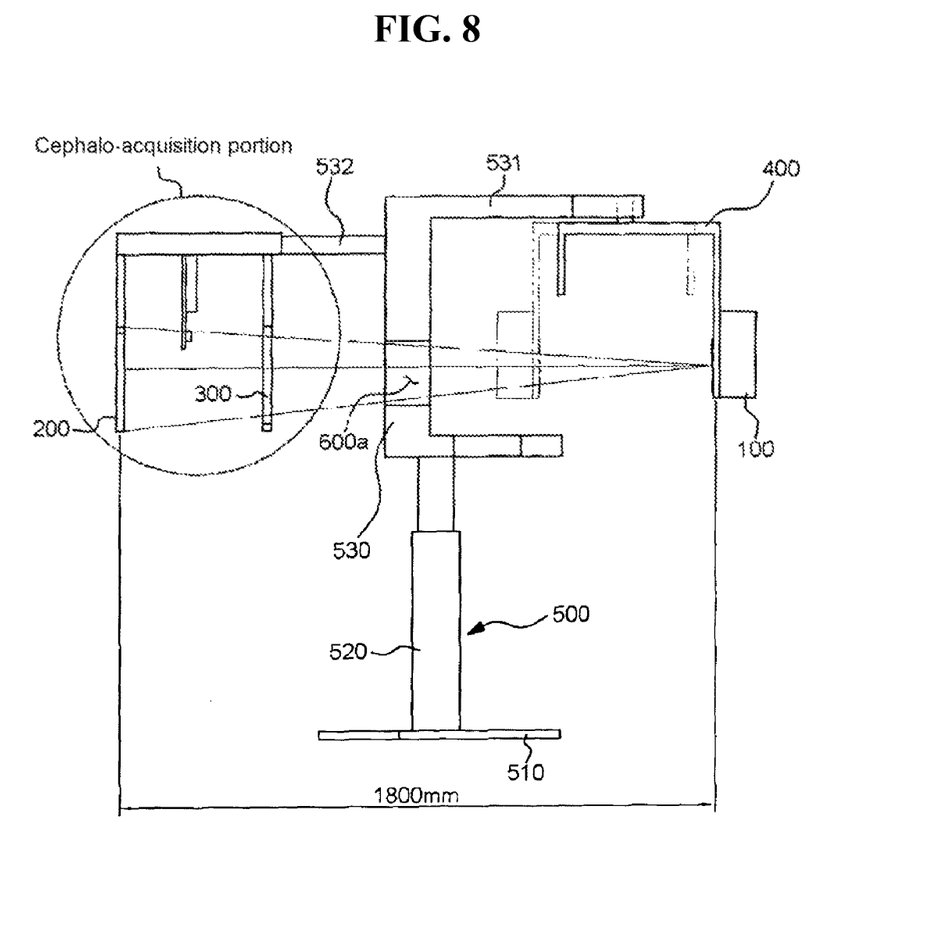
FIG. 8 is a front view of FIG. 7.
Figure 9:
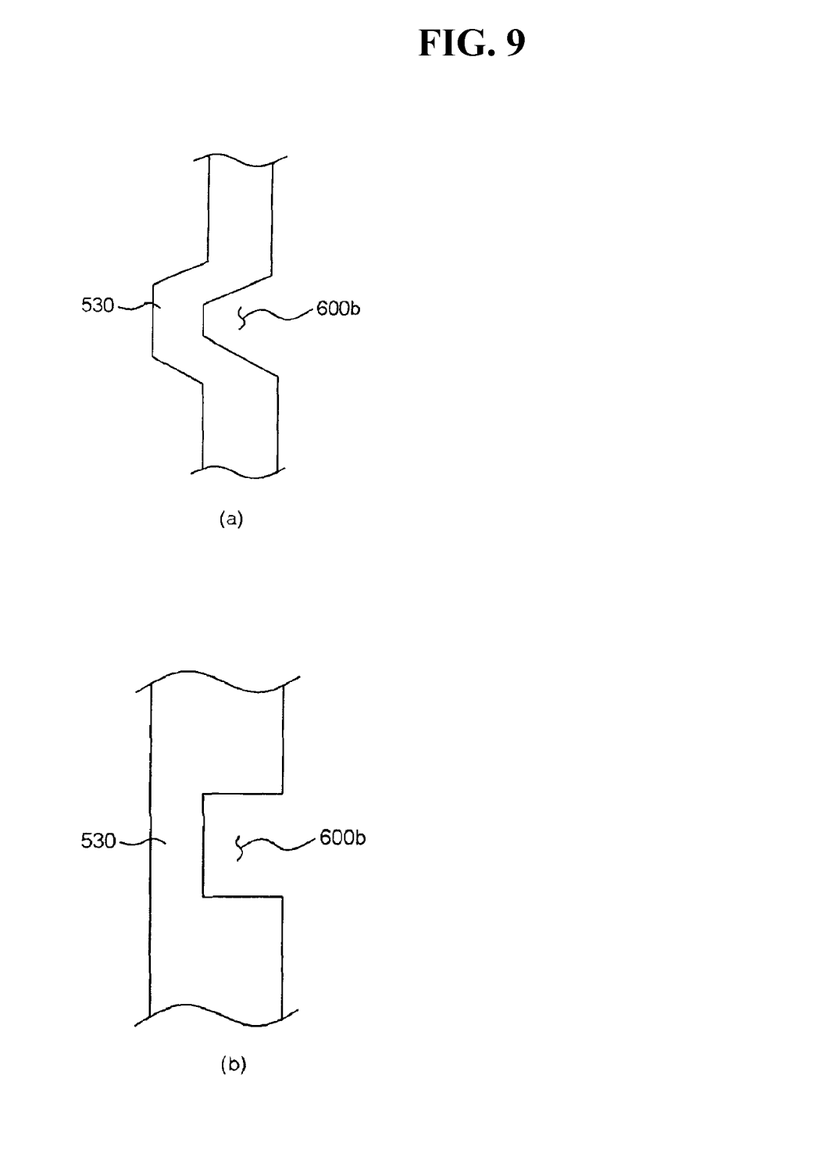

Referring to FIGS. 7 through 9, the X-ray photographing apparatus according to the present invention includes an X-ray generator 100 for generating X-rays, an X-ray detector 200 for detecting the X-rays discharged from the X-ray generator 100 and capturing an image of the head, a collimator 300 for permitting only a portion of the X-rays to pass through and blocking the rest X-rays, and a support means 500 for supporting the X-ray generator 100 and the X-ray detector 200 and varying the heights of the X-ray generator 100 and the X-ray detector 200.

Here, the X-ray generator 100 and the X-ray detector 200 are arranged facing each other at the respective left and right sides (in the drawings of the embodiment, the side of a cephalo-acquisition portion is defined as the left side, and the side of the X-ray generator 100 is defined as the right side) of the support means 500 for supporting the X-ray generator 100 and the X-ray detector 200 so as to achieve a weight balance.

In this case, the X-ray generator 100 and the X-ray detector 200 may be arranged to be placed on a straight line together with the support means 500. However, embodiments of the present invention are not limited thereto. That is, even though the X-ray generator 100 and the X-ray detector 200 are not precisely arranged on the straight line, they may be arranged within a range in which the weight balance is achieved.

The support means 500 has an X-ray path through which the X-rays generated by the X-ray generator 100 pass without interference.

The support means 500 includes a lift base 510, a lift guide 520 fixed to a top surface of the lift base 510, and a lift 530 that is supported by the lift guide 520, is installed to be elevatable in a lengthwise direction of the lift guide 520 and has an X-ray path through which the X-rays pass.

The X-ray path may be a through hole 600a (see portion "A" of FIG. 7 and FIG. 8) formed in a surface of the lift 530 that constitutes the support means 500. Unlike this, the X-ray path may be a kind of escape groove 600b (see FIG. 9) formed by a bent structure of the lift 530. According to the current embodiment, the lift 530 has support arms 531 and 532 that are integrally formed at the respective left and right sides of the lift 530 at a front end of the lift 530, and the X-ray generator 100 is pivotally installed at a front end of one-side support arm 531, and a cephalo-acquisition portion is installed at a front end of the other-side support arm 532.

In the cephalo-acquisition portion, the collimator 300 is coupled to a front side of the X-ray detector 200.

Also, the X-ray generator 100 is disposed at one end that is eccentric far away from a rotation center of a mount arm 400 that is rotatably installed at a front end of one-side support arm 531, and a panorama acquisition portion on which a panorama sensor 700 may be mounted, is disposed at the other end that is close to the rotation center of the mount arm 400.

An operation of the X-ray photographing apparatus having the above configuration according to the present invention will be described as below.

In the X-ray photographing apparatus according to the present invention, unlike the related art, the X-ray generator 100 and the X-ray detector 200 are arranged facing each other at the respective left and right sides of the lift 530 that constitutes the support means 500 so as to achieve the weight balance.

In this case, the X-ray generator 100 and the X-ray detector 200 are arranged on a straight line together with the lift 530 and are arranged facing each other at the respective left and right sides of the lift 530.

Thus, in the X-ray photographing apparatus according to the present invention, the weight balance is remarkably improved compared to that of the related art. Thus, the lift 530, of which an eccentric load having a very smaller value than that of the related art is considered, may be designed and applied so that the unit cost of components of the X-ray photographing apparatus can be reduced and production cost of a product of the X-ray photographing apparatus can be reduced.

As described above, if the X-ray generator 100, the X-ray detector 200 and the lift 530 are arranged to be placed on the straight line, while the X-rays discharged from the X-ray generator 100 proceed toward the X-ray detector 200, the X-rays are interfered with the lift 530. In the present invention, the X-ray path having an structure in which interference with the lift 530 is avoided, is formed, thus solving the problem.

In detail, the through hole 600a is formed in the surface of the lift 530 that constitutes the support means 500, as illustrated in FIGS. 7 and 8, or the lift 530 is formed as a kind of bent structure, thereby forming the escape groove 600b, as illustrated in FIGS. 9(a) and 9(b), thus forming a path through which the X-rays pass.

Of course, the escape groove 600b illustrated in each of FIGS. 9(a) and 9(b) has a different shape but is basically formed on the same principle.

In the X-ray photographing apparatus, the X-ray generator 100 configured together with the panorama acquisition portion is pivotally installed at the front end of the support arm 531. When the X-ray generator 100 is pivoted to be close to the lift 530, left and right widths of the X-ray photographing apparatus are greatly reduced.

This is because a rotation center of the mount arm 400 that is pivotally installed at the front end of the support arm 531 is placed at a position that is eccentric far away from the X-ray generator 100 in a lengthwise direction of the mount arm 400.

That is, the X-ray generator 100 is installed to be far away from the rotation center of the mount arm 400 that is pivotally installed at the front end of the support arm 531, whereas the panorama acquisition portion on which the panorama sensor 700 is mounted, is placed close to the rotation center of the mount arm 400 that is pivotally installed at the front end of the support arm 531.

Thus, in the X-ray photographing apparatus according to the present invention, when equipment for acquiring a cephalo-image operates normally, a sufficient distance from the X-ray generator 100 to the X-ray detector 200 is maintained at 1800 mm (this case corresponds to a solid state of FIG. 8). Instead, when the equipment does not operate, the X-ray generator 100 is placed at an inside of the support arm 521 so that the left and right widths of the X-ray photographing apparatus can be greatly reduced (this case corresponds to an imaginary line state of FIG. 8).

Accordingly, in the X-ray photographing apparatus according to the present invention, spatial utility of an installation space can be further improved.

While the invention has been shown and described with reference to certain exemplary embodiments thereof, it will be understood by those skilled in the art that various changes in form and details may be made therein without departing from the spirit and scope of the invention as defined by the appended claims.

INDUSTRIAL APPLICABILITY

According to the present invention, mechanical stability of an X-ray photographing apparatus that irradiates the head and/or teeth with X-rays and detects the X-rays, thus acquiring an image of the head and/or an image of the teeth, is improved. The X-ray photographing apparatus is made in a compact size as needed so that it is efficient to make the best use of an installation space in a dental clinic and thus the present invention contributes to popularization through wide spread and has a very high industrial applicability.

The invention claimed is:
1. An X-ray photographing apparatus comprising:
an X-ray generator for generating X-rays;
an X-ray detector for detecting the X-rays discharged from the X-ray generator;
a lift having a groove, through which X-rays pass, disposed between the X-ray generator and the X-ray detector; and
a collimator for permitting only a portion of the X-rays to pass through and blocking the rest X-rays, wherein
the apparatus further comprising a support means for supporting the X-rays generator and the X-ray detector and varying heights of the X-ray generator and the X-ray detector, wherein
the X-ray generator and the X-ray detector are arranged facing each other at respective left and right sides with respect to the support means for supporting the X-ray generator and the X-ray detector so as to achieve a weight balance, and
the support means configured to adjustably elevate the lift, wherein the X-ray generator, the lift, and the X-ray detector are arranged in parallel in horizontal direction based on the support means, and wherein
an X-ray path through which the X-rays generated by the X-ray generator pass without interference.

2. The X-ray photographing apparatus of claim 1, wherein the support means further comprises a lift base and a lift guide is fixed to a top surface of the lift base, and the lift is supported by the lift guide, and is adjustably elevatable in a vertical direction of the lift guide.

3. The X-ray photographing apparatus of claim 1, wherein the groove is formed by a bent structure of the lift through which X-rays pass.

4. The X-ray photographing apparatus of claim 1, wherein the lift has support arms are integrally formed at respective left and right sides of a front end of the lift, an X-ray generator is pivotally installed at a front end of one-side support arm of the left and right support arms, and a cephalo-acquisition portion is installed at a front end of the other-side support arm.

5. The X-ray photographing apparatus of claim 4, wherein the X-ray generator is disposed at one end that is eccentric far away from a rotation center of a mount arm that is rotatably installed at a front end of one-side support arm, and a panorama acquisition portion on which a panorama sensor is capable of being mounted, is disposed at the other end that is close to the rotation center of the mount arm.

6. An X-ray photographing apparatus comprising:
an X-ray generator for generating X-rays;
an X-ray detector for detecting the X-rays discharged from the X-ray generator;
a lift having a hole, through which X-rays pass, disposed between the X-ray generator and the X-ray detector; and
a collimator for permitting only a portion of the X-rays to pass through and blocking the rest X-rays, wherein
the apparatus further comprising a support means for supporting the X-rays generator and the X-ray detector and varying heights of the X-ray generator and the X-ray detector, wherein
the X-ray generator and the X-ray detector are arranged facing each other at respective left and right sides with respect to the support means for supporting the X-ray generator and the X-ray detector so as to achieve a weight balance, and
the support means configured to adjustably elevate the lift, wherein the X-ray generator, the lift, and the X-ray detector are arranged in parallel in horizontal direction based on the support means, and wherein
an X-ray path through which the X-rays generated by the X-ray generator pass without interference.

* * * * *